US006537274B1

(12) United States Patent
Katz

(10) Patent No.: US 6,537,274 B1
(45) Date of Patent: Mar. 25, 2003

(54) FIXATION SCREW, DETACHABLE PIN, GUIDE, AND FRAME

(75) Inventor: Richard Katz, Delmar, NY (US)

(73) Assignee: Biomet, Inc., Warsaw, IN (US)

( * ) Notice: Subject to any disclaimer, the term of this patent is extended or adjusted under 35 U.S.C. 154(b) by 168 days.

(21) Appl. No.: 09/672,337

(22) Filed: Sep. 28, 2000

(51) Int. Cl.[7] ......................... A61B 17/62; A61B 17/76
(52) U.S. Cl. .............................. 606/56; 606/59; 606/73
(58) Field of Search ............................ 606/56, 59, 72, 606/73, 61

(56) References Cited

U.S. PATENT DOCUMENTS

| | | | |
|---|---|---|---|
| 1,933,825 A | | 11/1933 | Sloan |
| 4,733,657 A | * | 3/1988 | Kluger ........................ 606/61 |
| 4,768,524 A | * | 9/1988 | Hardy ........................ 606/54 |
| 4,957,495 A | * | 9/1990 | Kluger ........................ 606/58 |
| 5,176,679 A | * | 1/1993 | Lin .............................. 606/61 |
| 5,382,248 A | * | 1/1995 | Jacobsen et al. ............. 606/60 |
| 5,478,340 A | * | 12/1995 | Kluger ........................ 606/61 |
| 5,688,285 A | * | 11/1997 | Yamada ..................... 606/104 |
| 5,690,633 A | * | 11/1997 | Taylor et al. ................ 606/73 |
| 5,702,389 A | * | 12/1997 | Taylor et al. ................ 606/54 |
| 6,402,757 B1 | * | 6/2002 | Moore, III et al. ........... 606/80 |

OTHER PUBLICATIONS

Ace Medical Company, Wire Tension Treatment of Complex Tibial Plateau & Pilon Fractures, Sales Representative's Extension believed published in United States in 1992.
Dr. James Nepola, Dynafix DFS Standard Fixator Application, publication on DFS Standard Fixator, believed published 6/99 in the United States.

* cited by examiner

Primary Examiner—Kevin Shaver
Assistant Examiner—David C. Comstock
(74) Attorney, Agent, or Firm—Liell & McNeil

(57) ABSTRACT

A method of treating a bone fracture includes a step of attaching a pair of bone fragments together with an internal screw. An outrigger pin is then attached to the internal screw. An alignment guide is positioned in the internal screw and in the outrigger pin. An external fixator frame is then attached to the outrigger pin. This structure combines the function of an internal screw with an external fixation pin in cases where there are at least two significant bone fragments that need to be compressed together and a need for external buttressing in order for proper healing of the bone fracture.

20 Claims, 4 Drawing Sheets

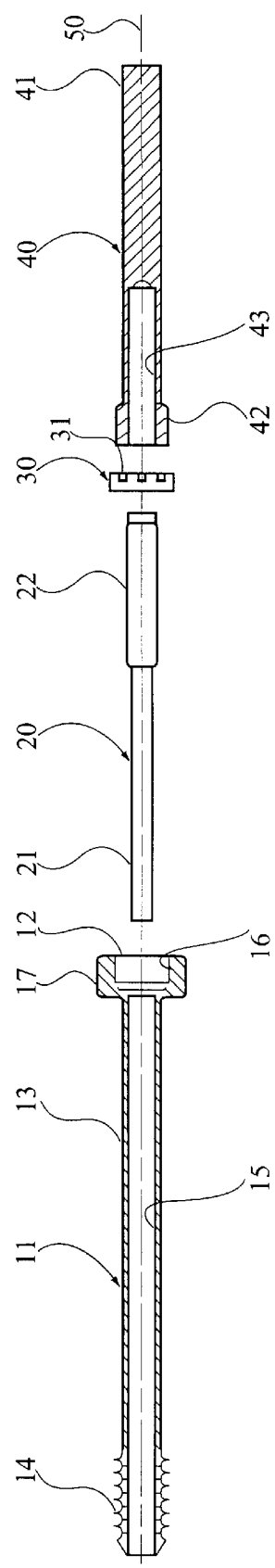
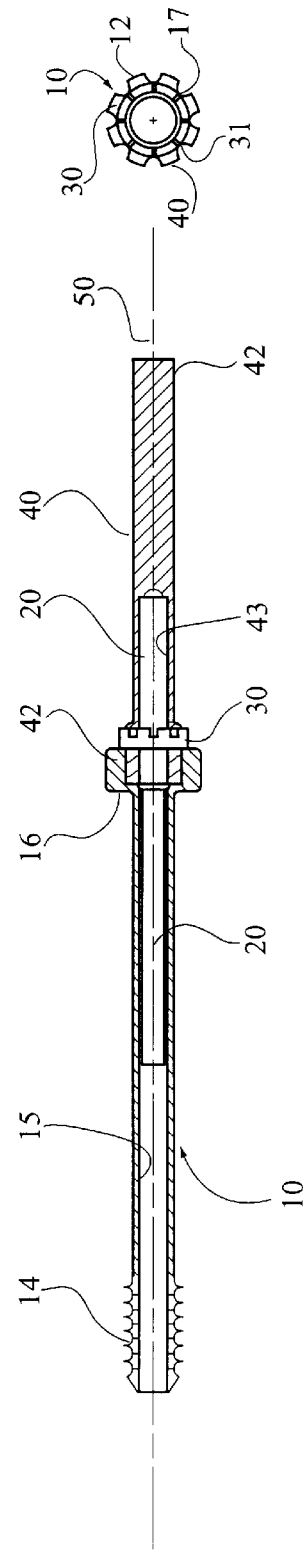
Figure 1
Figure 2
Figure 3

US 6,537,274 B1

FIXATION SCREW, DETACHABLE PIN, GUIDE, AND FRAME

TECHNICAL FIELD

The present invention relates generally to bone fracture fixation systems, and more particularly to a combined internal/external bone fixation screw.

BACKGROUND ART

Fractures of the proximal and distal tibia are often problematic to orthopedic surgeons. In the past, these fractures were treated with extensive open reduction combined with internal fixation. This included the use of lag screws combined with plates. As further knowledge of these fractures was gained, it was realized that the treatment of the soft issue played a vital role in the success of the treatment of these fractures. As a result, new fracture fixation systems were designed, including circular external fixator frames combined with internal lag screw fixation done percutaniously or through a very limited open incision.

As with the usage of all external fixation devices, there is a concern that infection can develop where the pins protrude through the skin. Thus, there is often a motivation to remove the external fixation device as quickly as possible as a risk of infection begins to rise rapidly with time after a number of weeks. Because of the relative complexity of external fixation systems, especially in cases where there is also a need for bone fragments to be compressed together with screws, there is often a reluctance among some orthopeadic surgeons to use both internal screws and external fixation devices. In many instances, this reluctance can sometimes result in a less than superior treatment of a certain class of tibial fractures.

The present invention is directed to these and other problems associated with complexity, flesibility and treatment quality associated with bone fractures that call for both internal compression and external fixation.

SUMMARY OF THE INVENTION

In one aspect of the Invention, a combined internal/external fixation screw includes an internal screw having a head and a shaft with external threads. An outrigger pin has one end that is detachable from the internal screw and an extension protruding away from the screw. The extension is sized and shaped for connection to an external fixator frame.

In another aspect of the invention, a method of treating a bone fracture includes a step of attaching a pair of bone fragments together with an internal screw. An outrigger pin is then attached to the internal screw. Finally, an external fixator frame is attached to the outrigger pin.

BRIEF DESCRIPTION OF THE DRAWINGS

FIG. 1 is an exploded partially sectioned side views of an internal/external fixation screw according to the present invention.

FIG. 2 is a partialiy sectioned side view of an assembled internal/external fixation screw according to the represent invention.

FIG. 3 is an end view of the internal/external fixation screw of FIG. 2.

DETAILED DESCRIPTION OF BEST MODE

Figure 4:
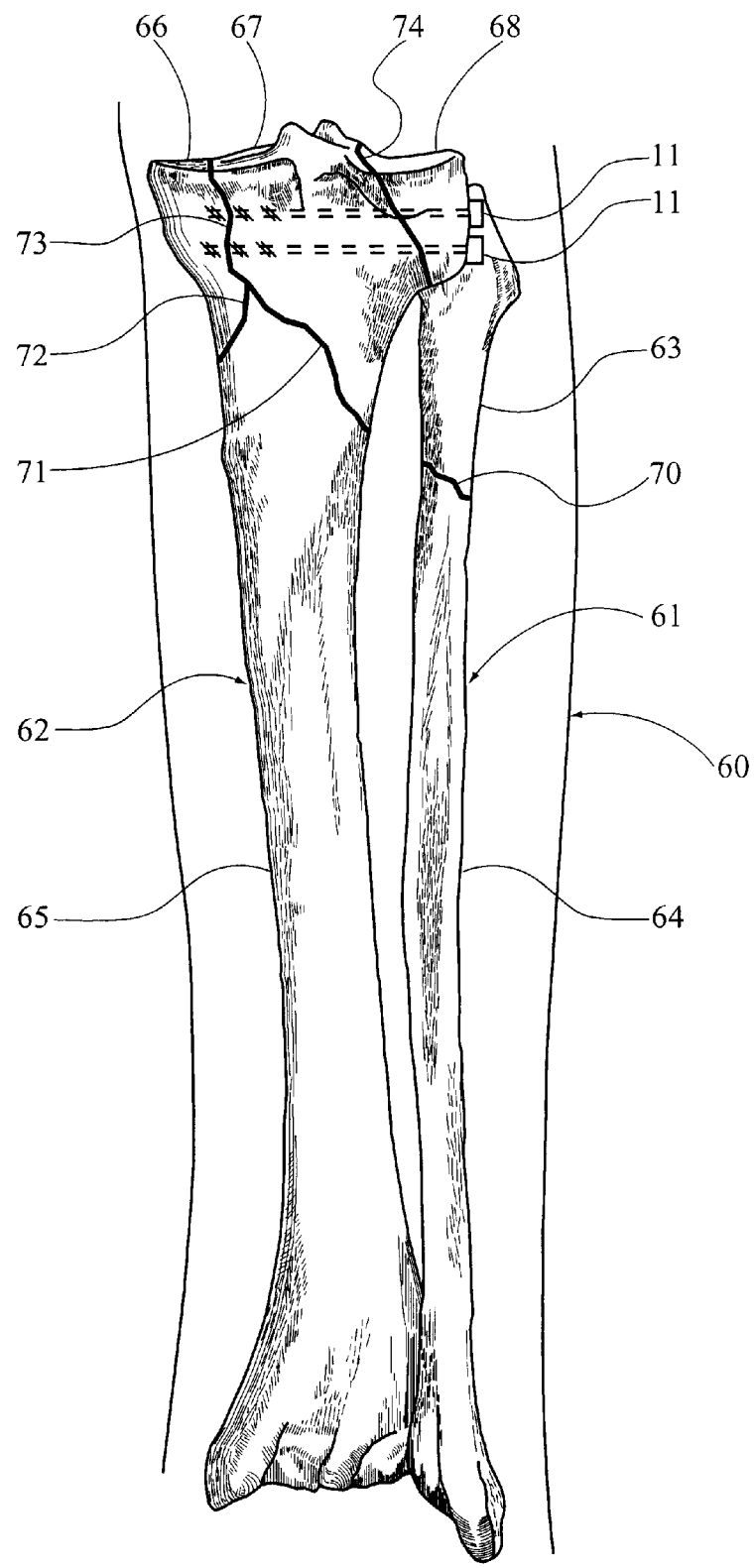
FIG. 4 is a front view of a fractured tibia and fibula with internal screws attached to compress the fractures in the tibia plateau region.

Referring now to FIGS. 1–3, a combined internal/external fixation screw 10 is shown in various views both assembled and disassembled. In particular, in the preferred version of the invention, the device includes an internal screw 11, an alignment pin 20, a jam nut 30 and an outrigger pin 40. Internal screw 11 includes a head 12 and a shaft 13 that extends from the head. A portion of shaft 13 includes external threads 14, which are preferably cancellous type threads, but cortical type threads could be suitable for some applications. Preferably, in the case of tibia fractures, internal screw 11 is substantially similar in shape to a conventional 6.5 millmeter cancellous, large screw. However, those skilled in the art will appreciate that screw 11 can take on a variety of shapes and sizes to suit a particular application. In the preferred version, screw 11 includes a cannulated passage 15 that permits the screws to be slid sever an appropriate guide pin for proper positioning and alignment with respect to the patient's bone fragments. The head portion 12 of screw 11 preferable includes a plurality of equally spaced rib indentations. These rib indentations enable the head to be coupled to an appropriately shaped tool so that the screw can be threaded into place in a conventional manner. Finally, head 12 includes a hollow interior with a set of internal threads 16 that allow the screw to be attached to the remaining portions of the device.

Outrigger pin 40 includes a set of external threads 42 that are sized and shaped to match the internal threads 16 of screw 11. These sets of matched internal and external threads provide the means by which the outrigger pin 40 is detachably attached to screw 11. However, those skilled in the art will appreciate other suitable couplers or attachment means that permit disattachment of the outrigger pin could be substituted for the illustrated threads. Outrigger pin 40 includes an extension 41 that is preferable sized and shaped for attachment to an external fixator frame in a conventional manner. Thus, extension 41 should have an appropriate length to extend outwardly to an external fixator frame when outrigger pin is attached to screw 11. Furthermore, extension 41 should have a material/cross sectional strength that permit it to support the anticipated stresses when the complete device is attached to a patient's bone and an external fixator frame. Although extension 41 could have any suitable cross sectional shape, it preferably is smooth and cylindrical in a manner similar to conventional pins for usage with external fixator frames. In order to better facilitate the attachment of outrigger pin 40 to screw 11 after screw 11 has been positioned within the patients body, outrigger pin 40 preferable defines an internal cavity 43 that is sized to receive a portion of an alignment pin 20.

Although not necessary, combined fixation screw 10 preferable includes an alignment pin 20 that includes a relatively small diameter first portion 21 that is sized to slide within cannulation passage 15, and an enlarged diameter second port or 22 that is preferably sized to be slideably received in internal cavity 43 of outrigger pin 40. Alignment pin 20 serves as a means of aiding in the alignment of outrigger pin 40 with screw 11 along a common centerline 50. Axial alignment can sometimes be problematic after screw 11 has been attached to the patients bone and the head is partially concealed by soft tissue.

In addition to the preferably inclusion of alignment pin 20, combined fixation screw 10 preferably includes a jam nut 30 with a set of internal threads that match the external threads 42 on outrigger pin 40. Jam nut 30 preferably includes a set of radially distributed castellation features 31 that permit mating to a suitable tool for rotation of the sane.

When assembled as shown in FIG. 2, outrigger pin 40 is partially threaded into head 12 of screw 11, but is held rigidly in place by advancing jam nut 30 into a position of abutting head 12 of screw 11. This permits the two primary components, screw 11 and outrigger pin 40 to be rigidly attached to one another by positioning the first tool on the rib 17 of head 12 and a second tool on the castellation features 31 of jam nut 30. This permits screw 11 and jam nut 30 to have counter torque's applied to one another without the risk of rotating screw 11 to an undesirable loosened or overly tight position with respect to the patent's bone. Likewise, when the two components are detached, the jam nut need only be loosened by torqueing against head 12 of screw 11, and then outrigger pin 40 can be easily unthreaded without applying any substantial torque to screw 11. In addition with assisting the alignment of outrigger pin 40 with screw 11 during attachment of the same, alignment pin 20 also can serve to carry some of the load that could otherwise cause undesirable stress in the attachment region of external threads 40 to internal threads 16.

In all cases of the invention, the combined device includes an internal screw with an outrigger pin that is detachable from the screw. The internal screw is preferably cannulated, but could be solid. The jam nut is preferably included but could be eliminated, in which case the outrigger pin would simply be screwed into the head of the internal screw until it seats in the same. Likewise, the alignment pin is preferred in order to assist in aligning the outrigger pin with the screw for attachment during an operation, but could be eliminated, in which case the outrigger pin would simply be initially threaded into internal screw in a conventional manner without alignment assistance.

In general, the present invention finds preferred application where there is both a pair of bone fragments that need to be compressed together, and the desire for buttressing or load supporting by an external fixation system. In cases of a severely commuted fracture, where there are no large fragments that could be compressed together, the present invention would be less preferable than other fixation techniques. The typical preferred application of the invention would be to the treatment of tibial plateau fractures and/or tibial plafond fractures. An open distal radius might be another fracture type where the present invention could find a preferred application. In most preferred applications, the combined internal/external fixation screw 10 of the present invention would be used in pairs. In other words, in order to perform in the preferred manner as a buttress with an external fixation system, at least two combined fixation screws 10 according to the present invention would be attached to the non-fractured portion of the tibia. Those skilled in the art will appreciate that the external buttressing function might fail in cases where the external fixation was only attached to one internal screw.

Figure 5:
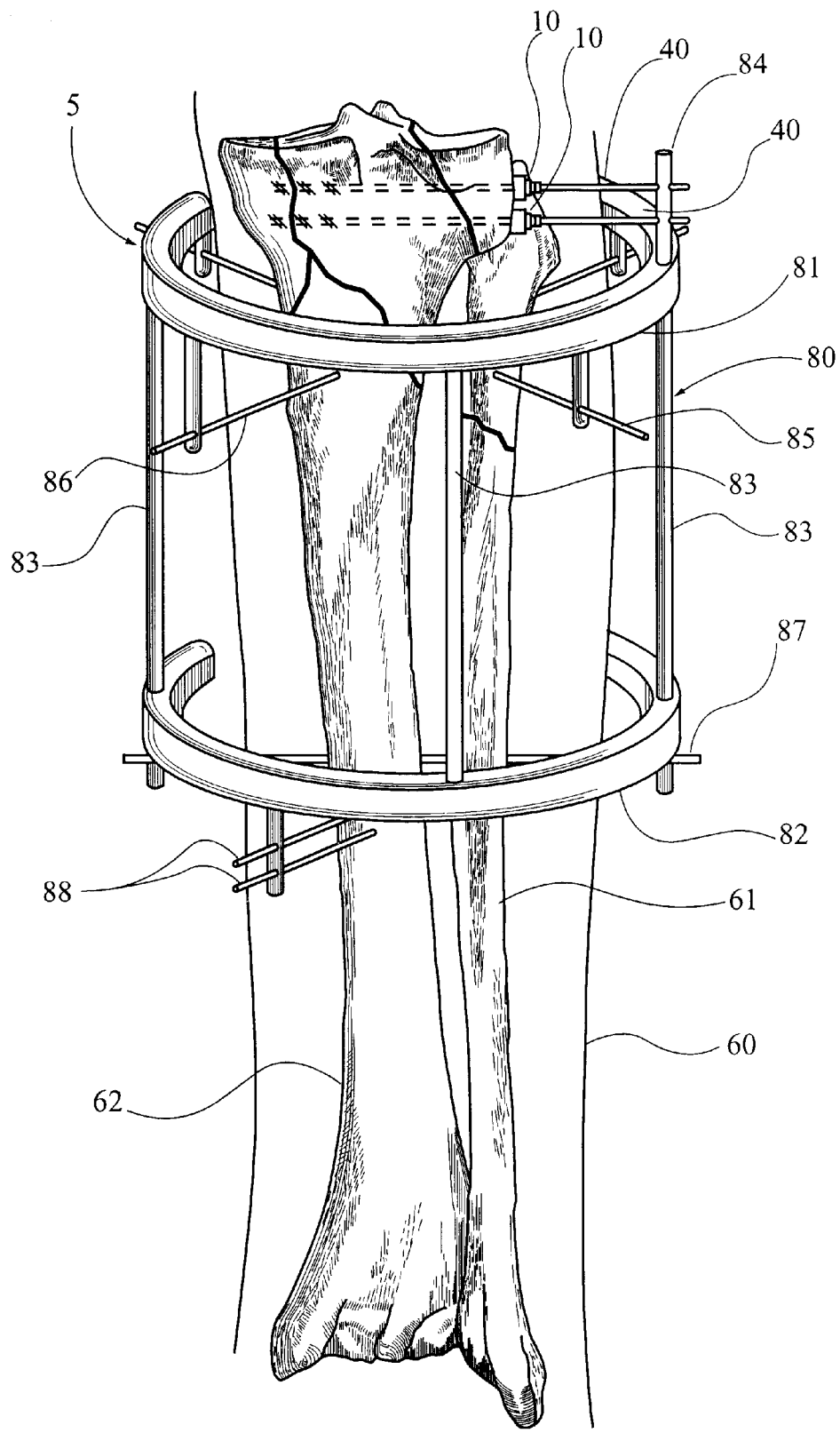
FIG. 5 is a front view of the fracture fixation system of the present invention attached to the tibia and fibula of FIG. 4.
Figure 6:
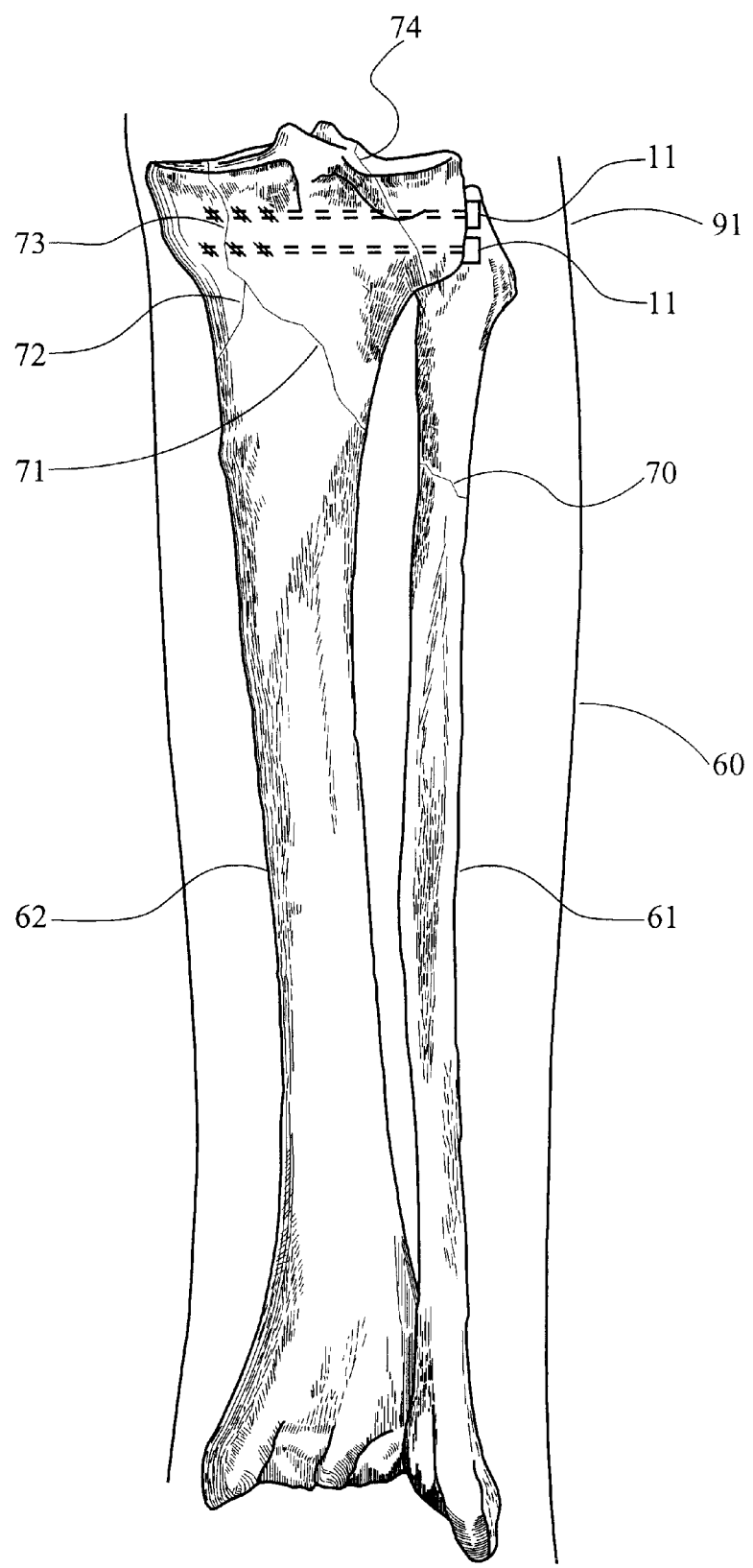
FIG. 6 is a front view of the tibia and fibula of FIGS. 4 and 5 after removal of the external fixator frame and associated pins.

Referring now to FIGS. 4–6, the preferred application of the present invention is illustrated with respect to treatment of an example tibial plateau fracture. In this particular example, the leg 60 of the patient includes both a fractured fibula 61 and a fractured tibia 62. A fibula fracture line 70 divides a first fibula bone fragment 63 from a second fibula bone fragment 64. Likewise, a first, second, third, and fourth tibia bone fragments 65–68 are separated from one another by fracture lines 71–74. In general, appropriate imaging should be used to assess the fracture locations and to plan proper placement of wires and screws. Those skilled in the art will recognize that most complex tibia fractures are often best approached through an anterior or anterolateral incision extending from the mid patella to the tibial tubercle. In general, the open incision should allow for visualization of the joint area.

After the tibial plateau is opened, the fracture fragments can be elevated as necessary. In many instances, the anterior portion of the lateral meniscus is detached and repaired after fixation of the fracture(s) is complete. In order to restore the articular surface of the tibial plateau, a pair of guide wires are positioned across the fracture in a conventional manner. In order to choose the appropriate length cannulated cancellous internal screw 11, a depth gage is preferably placed over the guide wires. The internal screws 11 are then slid over the guide wires and threaded into place to compress the bone fragments together in a conventional manner. Reduction of the fracture and screw placement and positioning are preferably verified using a appropriate imaging techniques.

After confirming the proper positioning of internal screws 11, the guide pins used for assisting there proper positioning can be removed. Next, an alignment pin 20 is inserted into the internal screw 11. Next, appropriately sized outrigger pins are chosen and a jam nut is partially threaded onto each outrigger pin. The outrigger pins are then slid over the exposed portion of the alignment pins until the external threads of the outrigger pin come in contact with the internal threads 16 in the head of internal screws 11. The outrigger pins are then rotated through several turns by hand until the jam nut begins to come into contact with head of internal screw 11. In order to avoid over tightening of internal screws 11, an appropriate tool can be mated to the indentation ribs 17 in head 12 to keep the same stationary during this portion of the procedure. Next, a tightening tool is mated to the castellation features of the jam nut, which is then torqued into place against the tool holding the internal screw in place. After tightening, the combined internal/external fixation screw behaves as a single rigid component that is ready for attachment to the external fixator frame 80.

The remaining portion of the fracture are buttressed and connected to the external fixator frame 80 in a conventional manner. In this case, an appropriate coupler 84 is mounted on a first ring 81, and serves as a means by which the outrigger pins 40 are attached to the external ring. In this example, the physician might choose to include a pair of full pins 85 and 86 that are oriented in a crosswise pattern and attached at there respective ends to first ring 81 in a conventional manner. Next, in order to avoid possible twisting and to further buttress the bone during healing, a second external ring 82 can be used. In this example, the second ring is coupled to the tibia 62 and fibula 61 using a full pin 87 and a pair of half pins 88. Finally, the rings 81 and 82 are connected and fixed in orientation relative to one another using a plurality of ring connectors 83.

In general, a fracture fixation system 5 of the present invention includes both the combined internal/external screws 10 of the present invention, the external fixator frame 80 and the various pins and couplers that are deemed necessary for the proper treatment of the fracture. Those skilled in the art will appreciate that the combined internal/external screw 10 of the present invention could be used, with little or no modification, with virtually any known external fixation frame.

FIG. 6 illustrates that, after some number of weeks, the external frame can be removed because the bone no longer needs the buttressing provided by the external frame because the fractures are partially healed. In this case, the outrigger pins, the alignment guide and jam nuts are detached from the internal screws, which are left in place. The incision 91 over the internal screws can then be closed, and the bone can be allowed to fully heal before later being reopened for removal of the screws, after healing is complete.

One of the major advantages of the present invention is its ability to provide an easier system to allow for fixation of proximal tibial and distal tibial articular fractures. The system can be relatively quick to apply, but still allow a surgeon to avoid the usage of plates in almost all situations, and lessen the complications known for plates in these areas. In addition, the fixation system of the present invention is simpler to apply than a conventional circular fixation system, which some surgeons are reluctant to use because of its complexity. Theoretically, the fixation system of the present invention could be applied to other areas such as the distal femur, distal radius, elbow, etc. with appropriately sized outrigger pins and internal screws. Furthermore, the modularity provided by the present invention provides the physician additional flexibility that can be exploited to the patients advantage during the surgical fixation. Thus, while the present invention has been illustrated with one example version of the combined internal/external fixation screw 10 in the context of a tibial plateau fracture and one kind of external fixator frame, those skilled in the art will appreciate that the various components that make up the present invention could come in a wide variety of shapes and sizes salted for a particular application. Thus, these skilled in the art will appreciate that various modifications could be made to the illustrated embodiment without departing from the intended scope of the invention, which is defined in terms of the claim set forth below.

What is claimed is:

1. A combined internal/external fixation screw comprising:
   an internal screw having a head and a shaft with external threads extending from said head;
   an outrigger pin having one end that is detachable from said internal screw and an extension protruding away from said end that is sized and shaped for connection to an external fixator frame; and
   an alignment guide at least partially positioned in each of said internal screw and said outrigger pin.

2. The fixation screw of claim 1 wherein at least one of said internal screw and said outrigger pin includes a portion of a coupling for attachment of said internal screw to said outrigger pin.

3. The fixation screw of claim 2 wherein said coupling includes one of said outrigger pin and said internal screw having a set of internal threads, and an other of said outrigger pin and said internal screw having a matched set of external threads.

4. The fixation screw of claim 3 wherein said internal screw includes said set of internal threads.

5. The fixation screw of claim 4 wherein said set of internal threads are located at least partially within said head.

6. The fixation screw of claim 4 including a jam nut threaded on said matched set of external threads and abutting said head of said internal screw.

7. The fixation screw of claim 1 wherein said internal screw is cannulated.

8. A combined internal/external fixation screw comprising:
   an internal screw having a head and a shaft with external threads extending from said head;
   an outrigger pin having one end that is detachable from said internal screw and an extension protruding away from said end that is sized and shaped for connection to an external fixator frame; and
   including an alignment pin with a portion positioned inside said internal screw, and a remaining portion positioned inside said outrigger pin.

9. A combined internal/external fixation screw comprising:
   an internal screw having a head and a shaft with external threads extending from said head;
   an outrigger pin having one end that is detachable from said internal screw and an extension protruding away from said end that is sized and shaped for connection to an external fixator frame;
   said head of said internal screw includes a set of internal threads, and said outrigger pin includes a matched set of external threads;
   a jam nut threaded on said external threads and abutting said head of said internal screw;
   said internal screw is cannulated; and
   an alignment pin with a portion positioned inside said internal screw, and a remaining portion positioned inside said outrigger pin.

10. A fracture fixation system comprising:
    an external fixator frame;
    an internal screw having a head and a shaft with external threads extending from said head;
    an outrigger pin at least partially positioned in said internal screw, and being connected to said external fixator frame; and
    an alignment guide at least partially positioned in each of said internal screw and said outrigger pin.

11. The fracture fixation system of claim 10 wherein said outrigger pin is threadedly attached to said internal screw.

12. The fracture fixation system of claim 10 wherein said internal screw is cannulated.

13. The fracture fixation system of claim 10 wherein said outrigger pin is threadably attached to said internal screw;
    said internal screw is cannulated; and
    said outrigger pin and said internal screw share a common centerline.

14. A method of treating a bone fracture comprising the steps of:
    attaching a pair of bone fragments together with an internal screw;
    positioning an alignment guide at least partially in each of an outrigger pin and said internal screw;
    attaching said outrigger pin to said internal screw; and
    attaching an external fixator frame to said outrigger pin.

15. The method of claim 14 wherein said step of attaching an outrigger pin includes the step of:
    threading one end of said outrigger pin into a head of said internal screw.

16. The method of claim 14 wherein said positioning step includes a step of inserting a guide pin partially into said internal screw after said step of attaching a pair of bone fragments; and
    threading a jam nut into a position abutting said head of said internal screw after said step of threading one end.

17. The method of claim 14 including the steps of:
    aligning said pair of bone fragments with a wire; and
    advancing said internal screw over said wire.

18. The method of claim 14 including the steps of:

allowing the bone to partially heal for a period of time after said step of attaching an external fixator frame;

detaching said external fixator frame from said outrigger pin; and detaching said outrigger pin from said internal screw; and closing an incision over said internal screw.

19. The method of claim 14 including the steps of:

attaching said pair of bone fragments together with a second internal screw;

attaching a second outrigger pin to said second internal screw; and attaching said external fixator frame to said second outrigger pin.

20. The method of claim 14 including the steps of:

aligning said pair of bone fragments with an alignment pin;

advancing said internal screw over said alignment pin;

said positioning step includes a step of inserting a guide pin partially into said internal screw after said step of attaching a pair of bone fragments;

threading one end of said outrigger pin into a head of said internal screw; and threading a jam nut into a position abutting said head of said internal screw after said step of threading one end.

* * * * *